(12) United States Patent
Morrissey

(10) Patent No.: US 7,494,782 B2
(45) Date of Patent: Feb. 24, 2009

(54) ASSAY FOR MEASURING FACTOR VIIA-ANTITHROMBIN COMPLEXES

(76) Inventor: James H. Morrissey, 2605 Willoughby Rd., Champaign, IL (US) 61822

( * ) Notice: Subject to any disclaimer, the term of this patent is extended or adjusted under 35 U.S.C. 154(b) by 701 days.

(21) Appl. No.: 10/481,345

(22) PCT Filed: Jul. 2, 2002

(86) PCT No.: PCT/US02/21081

§ 371 (c)(1),
(2), (4) Date: Feb. 27, 2004

(87) PCT Pub. No.: WO03/004694

PCT Pub. Date: Jan. 16, 2003

(65) Prior Publication Data

US 2004/0197842 A1    Oct. 7, 2004

Related U.S. Application Data

(60) Provisional application No. 60/302,867, filed on Jul. 3, 2001.

(51) Int. Cl.
*C12Q 1/56* (2006.01)
(52) U.S. Cl. .................. 435/13; 435/7.1; 435/7.92; 435/13; 435/287.2; 435/971; 435/973; 436/506; 436/517; 436/524; 436/525; 436/526; 436/527; 436/528; 436/529; 436/530; 436/531; 436/532; 436/533; 436/534; 436/538; 436/547; 436/548; 436/16; 436/69
(58) Field of Classification Search .............. 435/2, 435/4, 7.1, 7.5, 7.92, 7.94, 287.2, 967, 968, 435/971, 973, 3, 13; 436/517, 538, 548, 436/15, 69, 811
See application file for complete search history.

(56) References Cited

U.S. PATENT DOCUMENTS

| 5,248,596 A | 9/1993 | Esmon et al. ............. 435/7.92 |
| 5,741,658 A | 4/1998 | Morrissey .................. 435/23 |

(Continued)

FOREIGN PATENT DOCUMENTS

EP      0090505      10/1983

(Continued)

OTHER PUBLICATIONS

Kondo et al., Regulation of Factor VIIa Activity in Plasma: Evidence that Antithrombin III is the sole plasma protease inhibitor of human factor VIIa, Thrombosis Research, 46: 325-335 (1987).*

(Continued)

*Primary Examiner*—Gailene R Gabel
(74) *Attorney, Agent, or Firm*—Eugenia S. Hansen; Hemingway & Hansen, LLP

(57) ABSTRACT

A method for determining the concentration of factor VIIa-antithrombin complexes is disclosed which has application to estimating the level of intravascular exposure of tissue factor, assessing patient risk for hypercoagulation or other coagulopathies, and monitoring patients for factor VIIa-antithrombin complexes over time which can reveal changes in risk for hypercoagulation or other coagulopathies and/or effectiveness of anticoagulant therapy. Antibodies suitable for use in an in vitro assay for determining the concentration of factor VIIa-antithrombin complexes and methods for making the same are also disclosed.

16 Claims, 5 Drawing Sheets

U.S. PATENT DOCUMENTS 5,843,442 A     12/1998    Soule et al. ............... 424/145.1
6,492,185 B1*   12/2002    Kundu ......................... 436/518

FOREIGN PATENT DOCUMENTS

EP            0278776       8/1988

OTHER PUBLICATIONS

Goding, J.W., Monoclonal Antibodies: Principles and Practice. Academic Press, London (1983), pp. 56-97.*

Hui et al., Monoclonal antibodies to a synthetic fibrin-like peptide bind to human fibrin but not fibrinogen, Science 222: 1129-1132 (Dec. 9, 1983).*

Amiral, J. and Fareed, J. (1966). "Thromboembolic diseases: biochemical mechanisms and new possibilities of biological diagnosis," *Semin Thromb Hemost* 22 Suppl, 1:41-48.

Bauer, K.A. 1994. "New markers for in vivo coagulation," *Curr Opin Hematol* 1:341-346.

Bauer, K.A. 1999. "Activation markers of coagulation," *Baillieres Best Pract Res Clin Haematol* 12:387-406.

Cooper, J.A. et al. 2000. "Comparison of novel hemostatic factors and conventional risk factors for prediction of coronary heart disease," *Circulation* 102:2816-2822.

De Boer, J.P. et al. 1993. "Activation patterns of coagulation and fibrinolysis in baboons following infusion with lethal or sublethal dose of *Escherichia coli*," *Circ Shock* 39:59-67.

Drake, T.A. et al. 1993. "Expression of tissue factor, thrombomodulin, and E-selectin in baboons with lethal *Escherichia coli* sepsis," *Am J Pathol* 142:1458-1470b.

Gouin-Thibault, I. et al. 1995. "Measurement of factor Xa-antithrombin III in plasma: relationship to prothrombin activation in vivo," *Br J Haematol* 90:669-680.

Gouin-Thibault, I. and Samama, M.M. 1999. "Laboratory diagnosis of the thrombophilic state in cancer patients," *Semin Thromb Hemost* 25: 167-172.

Hamamoto, T. and Kisiel, W. 1998. "The effect of cell surface glycosaminoglycans (GAGS) on the inactivation of factor VIIa-tissue factor activity by antithrombin III," *Int J Hematol* 68:67-78.

Iversen, N. et al. 2000. "Tissue factor pathway inhibitor (TFPI) in disseminated intravascular coagulation: low levels of the activated factor X-TFPI complex," *Blood Coagul Fibrinolysis* 11:591-598.

Kondo, S. and Kisiel, W. 1987. "Regulation of factor VIIa in plasma: Evidence that antithrombin III is the sole plasma proteinase inhibitor of human factor VIIa," *Thromb Res* 46:325-335.

Lawson, J.H. et al. 1993. "Complex-dependent inhibition of factor VIIa by antithrombin III and heparin," *J Biol Chem* 268:767-770.

Miller, G.J. 2000. "Haemostatic factors in human peripheral afferent lymph," *Thromb Haemost* 83:427-432.

Morrissey, et al. 1987. "Molecular cloning of the cDNA for tissue factor, the cellular receptor for initiation of the coagulation protease cascade," *Cell* 50:129-135.

Morrissey, J.H. et al. 1993. "Quantitation of activated factor VII levels in plasma using a tissue factor mutant selectively deficient in promoting factor VII activation," *Blood* 81:734-744.

Morrissey, J.H. 1996. "Plasma factor VIIa: Measurement and potential clinical significance," *Haemostasis* 26:66-71.

Morrissey, J.H. 2001. "Tissue factor and factor VII initiation of coagulation," in *Hemostasis and Thrombosis: Basic Principles and Clinical Practice*, R.W. Colman et al. eds., Philadelphia: Lippincott Williams & Wilkins, pp. 89-101.

Neuenschwander P.F. et al. 1993. "Importance of substrate composition, pH and other variables on tissue factor enhancement of factor VIIa activity," *Thromb Haemost* 70:970-977.

Okugawa, Y. et al. 2000. "Increased plasma levels of tissue factor pathway inhibitor-activated factor X complex in patients with disseminated intravascular coagulation," *Am J Hematol* 65:210-214.

Rao, L.V.M. et al. 1993. "Binding of factor VIIa to tissue factor permits rapid antithrombin III/heparin inhibition of factor VIIa," *Blood* 81:2600-2607.

Takahashi, et al. 1991. "Activated factor IX-antithrombin III complexes in human blood: quantification by an enzyme-linked differential antibody immunoassay and determination of the in vivo half-life," *J Lab Clin Med* 118:317-325.

Taylor, F.B. et al. 1991. "Lethal *E. coli* septic shock is prevented by blocking tissue factor with monoclonal antibody," *Circ Shock* 33:127-134.

Taylor, F.B et al. 2001. "Two-stage response to endotoxin infusion into normal human subjects: Correlation of blood phagocyte luminescence with clinical and laboratory markers of the inflammatory, hemostatic response," *Crit Care Med* 29:326-334.

Esmon, CT. 2000. "Regulation of blood coagulation," *Bichimica et Biophysica Acta* 1477:349-360.

* cited by examiner

ASSAY FOR MEASURING FACTOR VIIA-ANTITHROMBIN COMPLEXES

CROSS-REFERENCE TO RELATED APPLICATION

This application claims benefit to U.S. provisional application No. 60/302,867 filed Jul. 3, 2001.

TECHNICAL FIELD OF INVENTION

This application relates to in vitro assays for blood coagulation disorders.

BACKGROUND

A number of clinical assays have been designed to measure the degree of turnover of the blood clotting system. These assays are routinely used to assess the severity of coagulopathies such as disseminated intravascular coagulation (DIC). Many of these assays are also being investigated for their utility in predicting hypercoagulable states that may predispose a person to developing deep vein thrombosis (DVT), heart attack, ischemic stroke, or other thrombotic and thromboembolic disorders. Examples of such assays are measurements of the plasma levels of fibrinopeptide A, thrombin-antithrombin complexes, prothrombin fragment 1+2, D-dimer, and factor VIIa (Amiral, J. and Fareed, J. (1966). "Thromboembolic diseases: biochemical mechanisms and new possibilities of biological diagnosis," *Semin Thromb Hemost* 22 Suppl, 1:41-48; Gouin-Thibault, I. and Samama, M. M. 1999. "Laboratory diagnosis of the thrombophilic state in cancer patients," *Semin Thromb Hemost* 25: 167-172; Morrissey, J. H. et al. 1993. "Quantitation of activated factor VII levels in plasma using a tissue factor mutant selectively deficient in promoting factor VII activation," *Blood* 81:734-744; and Morrissey, J. H. 1996. "Plasma factor VIIa: Measurement and potential clinical significance," *Haemostasis* 26:66-71). These assays permit insights into the degree of ongoing activation of the blood clotting system in vivo. For example, the levels of fibrinopeptide A and D-dimer reflect the degree to which fibrinogen is being converted into fibrin. The levels of thrombin-antithrombin complexes and prothrombin fragment 1+2 reflect the degree to which prothrombin is being converted to thrombin in vivo. One cannot measure thrombin activity levels in plasma directly because the active enzyme has an extremely short plasma half-life (owing to plasma's high content of protease inhibitors). Thus, the levels of thrombin-antithrombin complexes reflect the ongoing rate of thrombin activation in vivo because antithrombin (formerly known as antithrombin III or ATIII) is a major inhibitor of thrombin in plasma, and because these complexes have a much longer half-life in plasma than does thrombin. Similarly, prothrombin fragment 1+2 is released from prothrombin when it is activated to thrombin, and these fragments can circulate at measurable levels in plasma. For these reasons, measurements of either thrombin-antithrombin complexes or prothrombin fragment 1+2 in plasma are thought to reflect the ongoing rate of thrombin generation in vivo.

Assays to measure plasma markers of activation of other blood clotting factors have also been developed, in addition to those specific for the activation of thrombin. In the case of factors IX and X, as with thrombin, the active proteases (factors IXa and Xa) have very short half-lives in plasma, so it is not possible to measure their levels directly. However, as with prothrombin, assays have been developed to indirectly assess the degree of activation of factors IX and X. One set of methods involves measuring the plasma levels of activation peptides released from factors IX or X when they are converted to factors IXa or Xa. These activation peptides circulate with much longer half-lives than do the activated proteases themselves, and assays based on measuring the levels of such activation peptides have been developed and applied in a variety of epidemiologic studies (Bauer, K. A. 1994. "New markers for in vivo coagulation," *Curr Opin Hematol* 1:341-346; Bauer, K. A. 1999. "Activation markers of coagulation," *Baillieres Best Pract Res Clin Haematol* 12:387-406; and Cooper, J. A. et al. 2000. "Comparison of novel hemostatic factors and conventional risk factors for prediction of coronary heart disease," *Circulation* 102:2816-2822).

Another way to assess the ongoing rate of activation of factors IX or X is to measure the levels of circulating complexes of factor IXa or factor Xa with their plasma inhibitors. This has been done for factor IXa-antithrombin complexes (Takahashi, et al. 1991. "Activated factor IX-antithrombin III complexes in human blood: quantification by an enzyme-linked differential antibody immunoassay and determination of the in vivo half-life," *J Lab Clin Med* 118:317-325) and factor Xa-antithrombin complexes (Gouin-Thibault, I. et al. 1995. "Measurement of factor Xa-antithrombin III in plasma: relationship to prothrombin activation in vivo," *Br J Haematol* 90:669-680; Bauer, K. A. 1994. "New markers for in vivo coagulation," *Curr Opin Hematol* 1:341-346; and Bauer, K. A. 1999. "Activation markers of coagulation," *Baillieres Best Pract Res Clin Haematol* 12:387406). In addition, assays for measuring the circulating levels of complexes between factor Xa and tissue factor pathway inhibitor (TFPI) have also been developed (Okugawa, Y. et al. 2000. "Increased plasma levels of tissue factor pathway inhibitor-activated factor X complex in patients with disseminated intravascular coagulation," *Am J Hematol* 65:210-214; Iversen, N. et al. 2000. "Tissue factor pathway inhibitor (TFPI) in disseminated intravascular coagulation: low levels of the activated factor X-TFPI complex," *Blood Coagul Fibrinolysis* 11:591-598; Iversen, N. et al. 2000. "Tissue factor pathway inhibitor (TFPI) in disseminated intravascular coagulation: low levels of the activated factor X-TFPI complex," *Blood Coagul Fibrinolysis* 11:591-598; and Miller, G. J. 2000. "Haemostatic factors in human peripheral afferent lymph," *Thromb Haemost* 83:427-432).

Coagulation factor VII is converted to the activated form, factor VIIa, by proteolysis of a single peptide bond, and this is not associated with the release of an activation peptide (Morrissey, J. H. 2001. "Tissue factor and factor VII initiation of coagulation," in *Hemostasis and Thrombosis: Basic Principles and Clinical Practice*, R. W. Colman et al. eds., Philadelphia: Lippincott Williams & Wilkins, pp. 89-101). For this reason, it is not possible to monitor factor VII activation using an activation peptide assay, as has been done with prothrombin or factors IX or X. However, factor VIIa has a relatively long plasma half-life (about 2 hours), and so it has been possible to develop a clotting assay (based on a mutant form of tissue factor) that can specifically measure the levels of active factor VIIa in plasma (Morrissey, J. H. et al. 1993. "Quantitation of activated factor VII levels in plasma using a tissue factor mutant selectively deficient in promoting factor VII activation," *Blood* 81:734-744).

Measuring the plasma levels of factor VIIa are of interest because the blood clotting system is initiated when factor VII or VIIa binds to tissue factor (an integral membrane protein) on cell surfaces. The resulting membrane-bound complex of factor VIIa and tissue factor is the most potent known initiator of blood clotting. Tissue factor is normally present only on cells outside the vasculature, and it triggers blood clotting in normal hemostasis following vascular injury, thereby allowing blood to come into contact with tissue factor. Tissue factor expression can be induced on monocytes and endothelial cells by inflammatory mediators. Induced expression of tissue factor is thought to be responsible for the pathologic activation of blood clotting that triggers a number of thrombotic disorders (Morrissey, J. H. 2001. "Tissue factor and factor VII initiation of coagulation," in *Hemostasis and Thrombosis: Basic Principles and Clinical Practice*, R. W. Colman et al. eds., Philadelphia: Lippincott Williams & Wilkins, pp. 89-101).

Factor VIIa has a long half-life in plasma because it is essentially unreactive with any of the plasma protease inhibitors in the absence of its cofactor, tissue factor (Morrissey, J. H. 2001. "Tissue factor and factor VII initiation of coagulation," in *Hemostasis and Thrombosis: Basic Principles and Clinical Practice*, R W. Colman et al. eds., Philadelphia: Lippincott Williams & Wilkins, pp. 89-101). However, when factor VIIa binds to tissue factor, it becomes susceptible to inhibition both by antithrombin and TFPI. Interestingly, when factor VIIa bound to tissue factor reacts with antithrombin, the resulting factor VIIa-antithrombin (factor VIIa-AT) complexes lose affinity for tissue factor. Consequently these complexes, once formed, are released into solution (Hamamoto, T. and Kisiel, W. 1998. "The effect of cell surface glycosaminoglycans (GAGS) on the inactivation of factor VIIa-tissue factor activity by antithrombin III," *Int J Hematol* 68:67-78; Kondo, S. and Kisiel, W. 1987. "Regulation of factor VIIa in plasma: Evidence that antithrombin III is the sole plasma proteinase inhibitor of human factor VIIa," *Thromb Res* 46:325; Lawson, J. H. et al. 1993. "Complex-dependent inhibition of factor VIIa by antithrombin III and heparin," *J Biol Chem* 268:767-770; and Rao, L. V. M. et al. 1993. "Binding of factor VIIa to tissue factor permits rapid antithrombin III/heparin inhibition of factor VIIa," *Blood* 81:2600-2607).

Because factor VIIa is only susceptible to inhibition by antithrombin when it is bound to tissue factor, and because the resulting factor VIIa-AT complexes are released from tissue factor, the circulating levels of factor VIIa-AT reflect the degree of exposure of tissue factor to the blood. Such intravascular exposure of tissue factor is expected to result from inflammatory states and in fact has previously been shown to drive the lethal coagulopathy associated with sepsis (De Boer, J. P. et al. 1993. "Activation patterns of coagulation and fibrinolysis in baboons following infusion with lethal or sublethal dose of *Escherichia coli*," *Circ Shock* 39:59-67; Drake, T. A. et al. 1993. "Expression of tissue factor, thrombomodulin, and E-selectin in baboons with lethal *Escherichia coli* sepsis," *Am J Pathol* 142:1458-1470b; and Taylor, F. B. et al. 1991. "Lethal *E. coli* septic shock is prevented by blocking tissue factor with monoclonal antibody," *Circ Shock* 33:127-134). In addition, ongoing intravascular exposure of tissue factor, possibly due to chronic inflammatory conditions, may contribute to hypercoagulable states that could lead to the development of thrombotic diseases. For these reasons, it is of interest to be able to estimate the level of intravascular exposure of tissue factor.

It has now been found that measurable levels of factor VIIa-AT complexes are found in plasma and can be used to estimate the level of intravascular exposure of tissue factor. An ELISA assay has been developed for measuring the levels of factor VIIa-AT complexes in plasma Antibodies for use in the ELISA and methods of using the assay to assess patient risk or monitor anticoagulant therapy are also disclosed.

DETAILED DESCRIPTION

Figure 1:
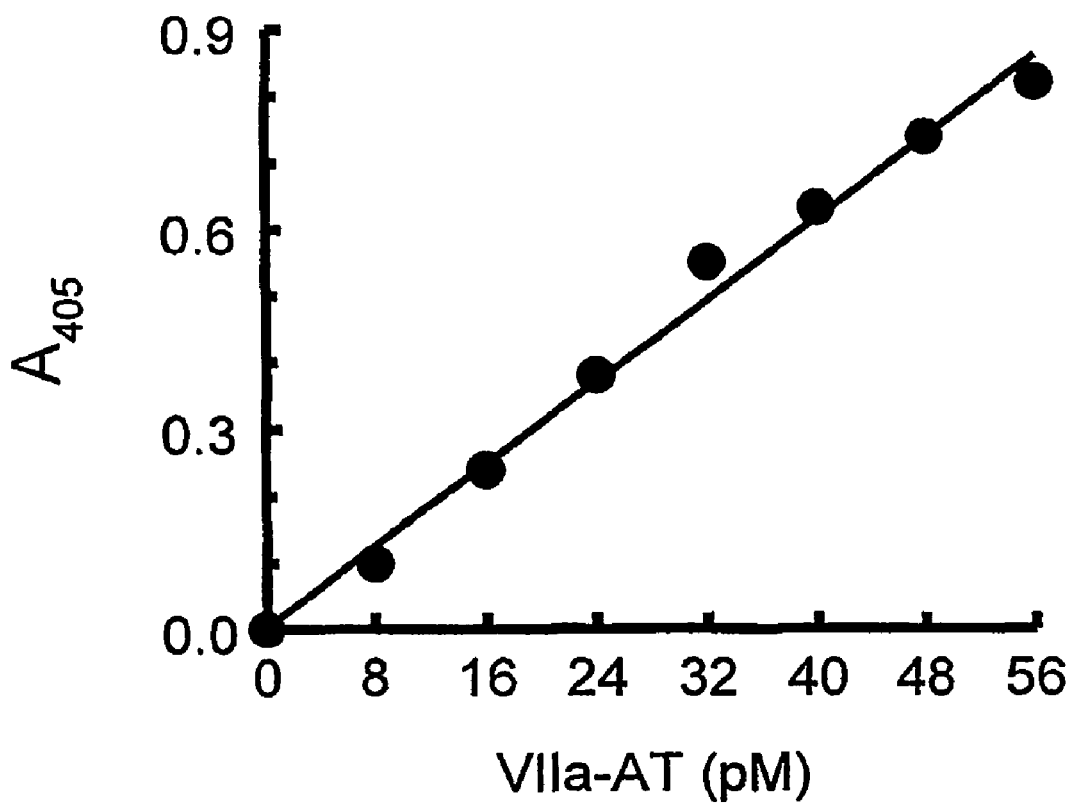
FIG. 1 depicts a typical factor VIIa-AT ELISA standard curve, using the methodology of Example 1.

Ongoing intravascular exposure of tissue factor resulting from vascular injury or a chronic inflammatory condition may contribute to hypercoagulable states that routinely lead to the development of a thrombotic disease. According to the present invention, a diagnostic assessment of a patient's risk of entering a hypercoagulable state can be made by measuring the amount of factor VIIa-AT complexes in the patient's plasma, and the level of circulating factor VIIa-AT complexes is deemed to reflect the degree of intravascular exposure of tissue factor. By monitoring a patient over time, an increase or decrease in the patient's level of circulating factor VIIa-AT complexes can be used to indicate an increased or decreased risk of entering a hypercoagulable state, respectively.

According to the present invention, measurable levels of circulating factor VIIa-AT complexes can be detected in patient plasma. The amount of factor VIIa-AT complexes in patient plasma can be measured by in vitro immunoassays. In such immunoassays, antibodies for detecting the presence of factor VIIa-AT complexes can be utilized in liquid phase or bound to a solid phase carrier. The antibodies against factor VIIa-AT complexes can be labeled using any variety of labels and methods of labeling known in the art, including but not limited to enzyme labels, radioisotopic labels, nonradioactive labels, fluorescent labels, toxin labels, and chemoluminescent labels. The binding of these labels to antibodies can be accomplished using techniques well known in the art (Harlow, E. and Lane, D. 1988. *Antibodies: A Laboratory* Manual, Cold Spring Harbor Laboratories, New York, pp. 319-358). Competitive radioimmunoassay methods can be used to measure factor VIIa-AT complexes by methods known in the art.

A preferred method of measuring factor VIIa-AT complexes is enzyme-linked immunosorbent assay (ELISA). For example, monoclonal antibodies capable of detecting factor VIIa-AT complexes can be utilized in an immunometric assay such as a two-site or sandwich assay. In a typical sandwich assay, a quantity of unlabeled antigen is bound to a solid support by means of a solid phase antibody and a quantity of detectably labeled soluble antibody is added to permit detection and/or quantitation of the complex formed between the solid phase antibody, antigen, and labeled antibody. (*Current Protocols in Immunology: Indirect Antibody-Sandwich ELISA to Detect Soluble Antigens*. John Wiley and Sons, New York, N.Y.; 1991; pp. 2.0.1-2.1.18). It is also contemplated that a reverse ELISA may be used—that is, the plates may be coated with antibodies to antithrombin and factor VIIa-AT complexes and detected with antibodies to factor VII/VIIa.

According to the present invention, factor VIIa-AT complexes in a patient plasma are preferably measured using a sandwich ELISA as illustrated in Example 1 or Example 2. In the sandwich assay, a primary capture antibody is utilized as the solid phase antibody. In a preferred embodiment, monoclonal or polyclonal antibodies, most particularly affinity purified to select for antibodies for the target antigen, for use as a primary capture antibody in the method of this invention are raised against factor VII or VIIa using standard procedures. Affinity purified polyclonal antibodies to VII/VIIa or monoclonal antibodies can be used. An appropriate antibody is selected by testing it for the properties required to function in the method of the invention, including the factor VIIa-AT ELISA procedure. The antibody selected as a primary capture antibody must not only have specificity for the target antigen and suitable affinity, but must exhibit calcium-independent binding (the ability to bind to factor VII/VIIa (even in the absence of calcium ions) and the ability to bind to factor VIIa (even when it is in complex with antithrombin)). These properties can be discerned by utilizing the testing procedures described herein. It should be noted that because Factor VII/VIIa binds multiple calcium ions, many antibodies raised against VII/VIIa will bind to this antigen only in the presence of calcium ions. In addition, the vast majority of antibodies raised against either factor VII or VIIa will bind equally well to both factor VII or VIIa.

Calcium-independent binding can be determined as follows. The monoclonal antibodies are initially screened for reactivity with factor VII or VIIa using standard procedures such as ELISA, radioimmunoassay (RIA) or other suitable technique. Whatever the method used, the screening for binding of antibody to factor VII must be done in the presence of a calcium chelating agent such as EDTA or EGTA (10 mM is generally sufficient), in order to ensure that the antibody binds to factor VII/VIIa in the absence of calcium ions. Only those antibodies whose binding is not diminished in the presence of EDTA are considered further.

The ability to bind in the presence of antithrombin can be determined as follows. Factor VIIa-antithrombin complexes (VIIa-AT) are prepared as described herein. Candidate anti-VII a antibodies are coated onto microtiter plates as described in the Example 1 and 2. Reactivity with factor VIIa-AT is detected using antibodies to antithrombin. Antibodies to factor VII/VIIa whose epitope is obscured when antithrombin binds to VIIa will fail to bind VIIa-AT complexes and will therefore fail to give a positive signal in this ELISA. A positive signal is an increase in signal above background. Background is determined by using an irrelevant control antibody bound to the plates.

Antibodies to AT are commercially available from a number of sources, and a suitable one may be selected by a test similar to the one provided above for binding to factor VIIa-AT complexes, except that antibodies to factor VIIa/VII are used to test whether the epitope of antithrombin is obscured and cannot thereafter bind to VIIa-AT complexes. As shown in Example 1, an exemplary capture antibody is an IgG1 murine monoclonal antibody against human factor VII designated as Antibody #1172 (hybridoma cells deposited with the American Type Culture Collection, 10801 University Boulevard, Manassas, Va. under Depositor's Designation #1172 and given ATCC No. PTA-3497), which binds to factor VII or VIIa in a calcium-independent manner, and because its epitope is not occluded when factor VIIa reacts with antithrombin, Antibody #1172 also recognizes factor VIIa-AT complexes. The primary capture antibody can also be an antibody capable of recognizing the AT portion of the factor VIIa-AT complex, provided that its epitope is not occluded when factor VIIa reacts with antithrombin to form factor VIIa-AT complexes. It is contemplated that changes to the primary capture antibody can be made and the function in the assay preserved. For example, Fab or Fab'$_2$ fragments may be prepared using known methodology and such fragments used in the assay.

The primary capture antibody is coated onto a suitable assay container such as a polystyrene 96-well plate. One could also use alternative methods of immobilization such as biotinylating the antibody and capturing it on plates using immobilized avidin or streptavidin. When the sandwich is reversed, one could also detect biotinylated #1172 binding using a suitably tagged avidin or streptavidin. The plate may, if desired, be blocked against non-specific binding by any acceptable means known in the art, preferably by nonfat skim milk, then washed with a suitable buffer to remove any unbound capture antibody. An example of using the blocking technique is provided in Example 1, and an example without the blocking technique is provided in Example 2.

According to the assay of the present invention, the amount of factor VIIa-AT complexes in either patient plasma or any other preparation is quantitated by comparison to a standard curve prepared by simultaneously assaying known concentrations of factor VIIa-AT complexes. To prepare a patient sample, a small amount of blood is drawn by venipuncture using standard hematologic techniques into an anticoagulant, from which the plasma is prepared by centrifugation. The patient's plasma can be anticoagulated with either citrate, EDTA, or other calcium-chelating agent. The resulting platelet-poor plasma is then preferably serially diluted 10- to 40-fold, more preferably 20- to 40-fold, with a suitable buffer and aliquots of each dilution are added to wells in the plate to provide a range of final concentrations.

To prepare the standard curve, known concentrations of factor VIIa-AT complexes are preferably generated in vitro using purified proteins. Exemplary final concentration ranges are 0, 20, 40, 60, 80, and 100 pM per well; more preferably, 0, 8, 16, 24, 32, 40, 48 and 56 pM per well. Examples 1 and 2 provide exemplary in vitro methods for obtaining factor VIIa-AT complexes. In general, factor VIIa (50-100 nM, preferably 100 nM) is combined with tissue factor (100-150 nM, preferably 150 nM in terms of recombinant soluble tissue factor) to form factor VIIa-tissue factor complexes which are then reacted with antithrombin (100-750 nM, preferably 400 nM) and heparin to form factor VIIa-AT complexes. The concentrations of tissue factor and antithrombin need to be in excess compared to the concentration of Factor VIIa. Factor VIIa can be obtained by converting isolated factor VII to factor VIIa according the procedures outlined in U.S. Pat. No. 5,741,658, which is herein incorporated by reference. Preferably, purified recombinant human factor VIIa is utilized. Recombinant factor VIIa can be generated according to any means known in the art or commercially obtained. The tissue factor useful in generating the factor VIIa-tissue factor complexes can be either full length or truncated, isolated or recombinant (European Patent Application No. 0278776; and Morrissey, et al. 1987. "Molecular cloning of the cDNA for tissue factor, the cellular receptor for initiation of the coagulation protease cascade," *Cell* 50:129-135), wild-type or modified. Soluble tissue factor can be obtained from Diagnostica Stago, Inc., Parsippany, N.J. Antithrombin (also known as antithrombin III or ATIII) can be isolated or recombinant (European Patent No. 0090505). Commercial sources for antithrombin III isolated from pooled fresh frozen human plasma include American Diagnostica, Inc., Greenwich, Conn. and Haematologic Technologies, Inc., Essex Junction, Vt. Any commercial source of heparin with anticoagulant properties can be used in the present invention. Verification of conversion to factor VIIa-AT complexes can be accomplished by any means known in the art. Example 2 gives an exemplary procedure whereby the factor VIIa enzymatic activity of the factor VIIa-tissue factor complexes and the factor VIIa-AT complexes are compared, with the formation of factor VIIa-AT complexes being indicated by a sufficient loss of factor VIIa enzymatic activity and the concentration of factor VIIa-AT complexes associated with the starting concentration of factor VIIa. The resulting factor VIIa-AT standard is then serially diluted with a suitable buffer and aliquots of each dilution are added to wells in the plate to provide final concentrations in the pM range.

Following incubation under conditions to permit reaction between the primary capture antibody and factor VIIa-AT complexes and washing with appropriate buffer, the plate is treated with a secondary antibody capable of binding to either the antithrombin or factor VIIa portion of factor VIIa-AT complexes which binds the opposite portion of the complex from that bound by the capture antibody (i.e., if the capture antibody is bound to the factor VIIa portion, a secondary antibody capable of binding to the antithrombin portion is used; and if the capture antibody is bound to the antithrombin portion, a secondary antibody capable of binding to the factor VIIa portion is used). Specificity for factor VIIa-AT complexes is achieved by using the combination of a primary capture antibody which binds to either factor VII/VIIa or antithrombin and a secondary antibody which binds to the opposite portion of the complex. The secondary antibody can be labeled for detection by means of enzyme labels, radioisotopic labels, nonradioactive labels, fluorescent labels or other dyes, toxin labels, or chemoluminescent labels. After washing with an appropriate buffer, the plate is examined for bound labeled secondary antibody, and the amount of bound labeled secondary antibody in each well is quantitated by means known in the art for the specific type of label used.

A preferred method uses a secondary antibody detectable by means of a chromogenic substrate assay. An exemplary secondary antibody for this assay is a polyclonal antibody raised against human antithrombin in an animal source for which an anti-IgG is readily available (e.g., a polyclonal antibody raised in rabbits against human antithrombin). As shown in Example 1, primary Antibody #1172 will capture multiple different forms of factor VII or VIIa, and the secondary rabbit anti-antithrombin antibody will only recognize antithrombin, and the only antithrombin that will be present is antithrombin that has reacted previously with factor VIIa. Any capture antibody which is pretested according to the methods provided herein will work in the assay as well.

After washing with an appropriate buffer, the plate is treated with a tertiary antibody which recognizes the secondary antibody; thus, the tertiary antibody will only bind to plates on which the secondary antibody has been previously bound. In the chromogenic substrate assay, the tertiary antibody has previously been conjugated to an enzyme capable of interacting with a chromogenic substrate to form a measurable spectrophotometric change, many of which are well known in the art. In Example 1, the tertiary antibody is a donkey antibody to rabbit IgG (preferably purified to minimize cross-reactivity with mouse IgG) which has been conjugated to the enzyme alkaline phosphatase. The tertiary donkey antibody to rabbit IgG conjugated to alkaline phosphatase will only bind to the secondary rabbit anti-antithrombin antibody previously bound on the plate.

After final washing with an appropriate buffer, the plates are treated with the appropriate chromogenic substrate, and the enzyme which was conjugated to the tertiary antibody, if present, will react with the chromogenic substrate to form a measurable spectrophotometric change which is proportional to the amount of substrate converted by the available enzyme. The spectrophotometric change in each well is measured either visually or by one of many spectrophotometric reading devices known in the art. In Example 1, the plates are treated with alkaline phosphatase substrate p-nitrophenylphosphate p-NPP) in a suitable buffer. The absorbance of light at 405 nm is then measured using a microplate reader.

Figure 5:
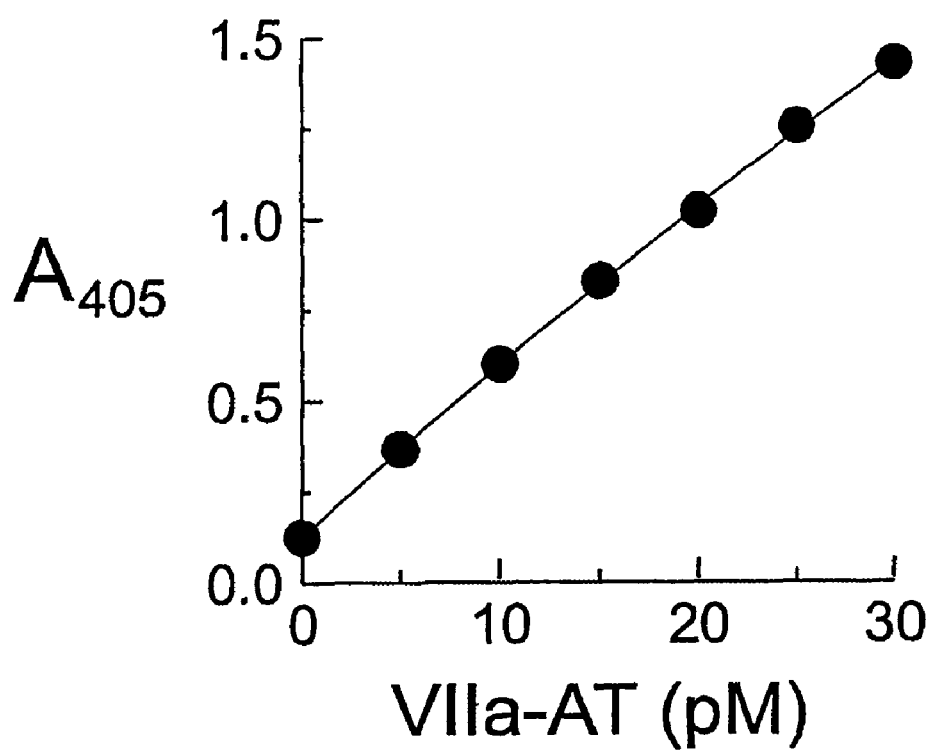
FIG. 5 depicts a typical standard curve for the ELISA assay pursuant to the methodology of Example 2.

Using the results from either the labeled secondary antibody or the chromogenic substrate assay, a standard curve is prepared using the series of factor VIIa-AT standards, and the levels of the factor VIIa-AT complexes in the patient plasma is measured from its labeled value by reference to the standard curve. An example of a standard curve generated according to the method in Example 1 for factor VIIa-AT complexes is given in FIG. 1, and a standard curve generated according to the method in Example 2 is given in FIG. 5. Control experiments have shown that the ELISA procedure presented in Example 1 is specific for factor VIIa-AT complexes, as complexes of factor Xa and antithrombin failed to give a signal with this ELISA.

As stated earlier, various techniques may be used in lieu of an ELISA assay and such techniques are well known in the art. The feature that is to be employed in all such techniques is the generation of a standard curve for known concentrations of factor VIIa-AT complexes which is a unique feature of the instant invention. In addition, the calcium independent nature of the antibody to factor VII/VIIa and the ability of said antibody to bind to factor VIIa even when complexed to AT is a novel feature of this invention.

Figure 2:
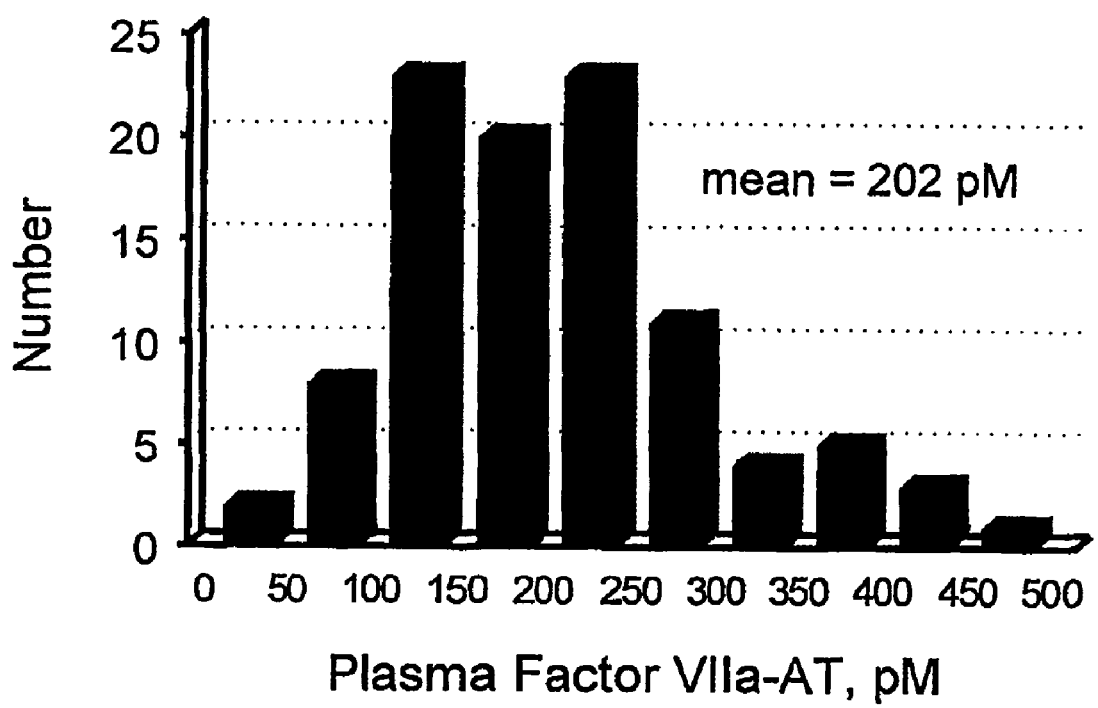
FIG. 2 is a histogram of the distribution of factor VIIa-AT levels in the plasma of 100 normal volunteers.

Using the factor VIIa-AT ELISA presented in Example 1, we measured the levels of factor VIIa-AT complexes in 100 normal blood donors. All of the donors had detectable factor VIIa-AT complexes in their plasma, with a mean level of 202 pM and a relatively broad range (FIG. 2, Table I). Interestingly, the mean levels of factor VIIa-AT complexes in plasma represented about 2% of the total factor VII, while the mean levels of active factor VIIa represented about 0.7% of the total factor VII (Morrissey, J. H. et al. 1993. "Quantitation of activated factor VII levels in plasma using a tissue factor mutant selectively deficient in promoting factor VII activation," *Blood* 81:734-744). Thus, factor VIIa-AT complexes exist in plasma at a level that is about three-fold

TABLE I

Factor VII Levels in Plasma

| Species | Plasma Concentration | % of Total Factor VII |
|---|---|---|
| Total Factor VII | 500 ng/ml = 10 nM | 100% |
| Active Factor VIIa | 3.6 ng/ml = 72 pM | 0.7% |
| Factor VIIa-AT Complexes | 10.1 ng/ml = 202 pM | 2.0% | higher than that of active factor VIIa. This suggests that ongoing turnover of factor VIIa through the tissue factor-catalyzed interaction with antithrombin may represent a major pathway by which factor VIIa levels are controlled. This differs from conventional wisdom, which indicates that TFPI is the major plasma inhibitor of factor VIIa.

Figure 3:
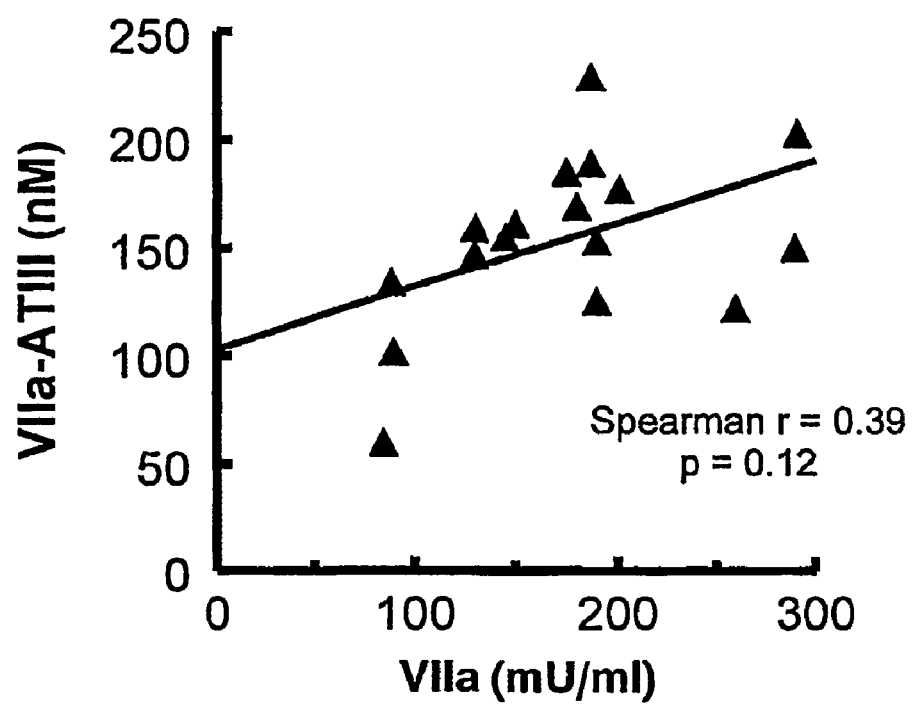
FIG. 3 depicts the relationship between plasma levels of active factor VIIa and factor VIIa-AT complexes.

Plasma levels of factor VIIa and factor VIIa-AT complexes were measured in identical samples from 17 normal donors (FIG. 3). There was a weakly positive relationship between active factor VIIa levels and factor VIIa-AT levels, but it was not statistically significant (p=0.12). This indicates that factor VIIa-AT levels are not strongly tied to active factor VIIa levels. This is probably due to different levels of exposure of active tissue factor to the blood in different individuals.

Figure 4:
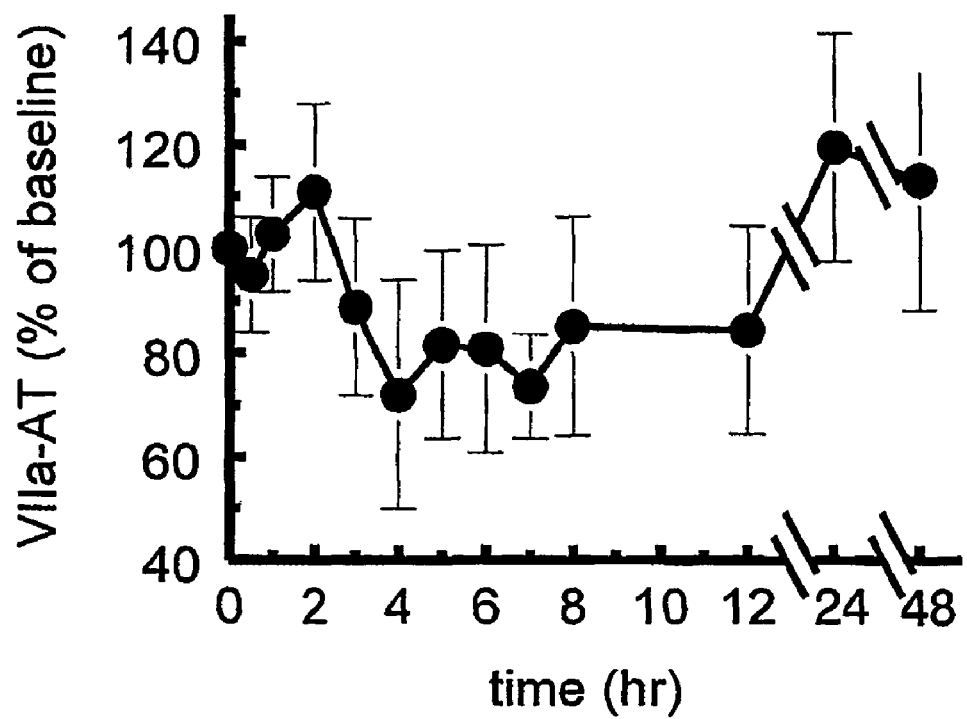
FIG. 4 depicts factor VIIa-AT complexes measured in the plasma of normal volunteers treated with low levels of bacterial endotoxin (LPS). These blood samples were from the published endotoxin infusion study of Taylor et al. (Taylor, F. B et al. 2001. "Two-stage response to endotoxin infusion into normal human subjects: Correlation of blood phagocyte luminescence with clinical and laboratory markers of the inflammatory, hemostatic response," *Crit Care Med* 29:326-334).

Plasma levels of factor VIIa-AT complexes changed substantially following intravenous administration of low dose bacterial endotoxin to normal volunteers (Table II and FIG. 4). This almost certainly reflects the increase in exposure of tissue factor in blood due to induction of tissue factor expression by circulating monocytes.

Changes in levels of intravascular exposure to tissue factor can be measured by monitoring the change in plasma levels of factor VIIa-AT complexes using the assay of the present invention. The method can be used to monitor patients in which activation of the clotting cascade is suspected, and that elevations in VIIa-AT levels above the patient's baseline would be indicative of intravascular activation of the clotting system. Patients in which this might be used could include patients with (or suspected of

TABLE II

Levels of Factor VIIa-AT Complexes After Exposure to Endotoxin

| Time (hours) | VIIa-AT(% of patient's baseline value) |
|---|---|
| 0 | 100 |
| 0.5 | 95 |
| 1.0 | 103 |
| 2.0 | 111 |
| 3.0 | 89 |
| 4.0 | 72 |
| 5 | 82 |
| 6 | 81 |
| 7 | 74 |
| 8 | 85 |
| 12 | 84 |
| 14 | 120 |
| 16 | 118 | having) sepsis, septic shock, ARDS (acute respiratory distress syndrome), cancer, deep vein thrombosis, myocardial infarction, ischemic stroke, pulmonary embolism, obstetric complications (including pre-eclampsia and eclampsia), and coronary artery disease.

In another embodiment, VIIa-AT values can be used as a sensitive way of monitoring the efficacy of anticoagulant therapy. This would include oral anticoagulants (warfarin and related compounds), and also heparin and heparin derivatives. In yet another embodiment, VIIa-AT values can be used to monitor the efficacy of novel anticoagulants, especially those that target factor VIIa or the tissue factor-factor VIIa complex.

EXAMPLE 1

ELISA Assay for Measuring the Level of Factor VIIa-AT Complexes in Plasma Using p-NPP Substrate (With Use of Blocking Agent)

The ELISA assay was used to measure the concentration of factor VIIa-antithrombin (factor VIIa-AT) complexes in human plasma and other samples.

Preparation of Factor VIIa-AT Complexes for Standardizing the Factor VIIa-AT ELISA A 1.1 ml solution of 100 nM factor VIIa [Factor VIIa (recombinant); catalog #407recB; American Diagnostica, Inc., Greenwich, Conn.] and 150 nM sTF [recombinant soluble tissue factor protein produced by methods known in the art] was prepared in HBSA/calcium [HBSA/calcium: 30 mM Hepes buffer, pH 7.4, 100 mMNaCl, 5 mM $CaCl_2$, 0.1% w/v bovine serum albumin, and 0.1% w/v sodium azide and stored at 4° C.].

A 0.1 ml aliquot was removed and held on ice to form factor VIIa-sTF complexes.

To the remaining 1.0 ml reaction mixture, heparin (catalog #H3393; Sigma Chemical Co. St. Louis, Mo.) was added to a final concentration of 1 unit/ml and Antithrombin (formerly called Antithrombin III; catalog #HCATIII-0120; Haematologic Technologies, Inc., Essex Junction, Vt.) to a final concentration of 300 nM. The mixture was incubated at 37° C. for 60 minutes and then placed on ice to form the factor VIIa-AT standard (factor VIIa-sTF treated with heparin and antithrombin).

A small aliquot of both the factor VIIa-sTF complexes and factor VIIa-AT standard was removed, and the remaining factor VIIa enzymatic activity was measured (at a final concentration of 5 nM factor VIIa), using Chromozym t-PA substrate (catalog #1 093 037, Roche Diagnostics, Inc., Indianapolis, Ind.) according to the procedure given by Neuenschwander, et al. (Neuenschwander P. F. et al. 1993. "Importance of substrate composition, pH and other variables on tissue factor enhancement of factor VIIa activity," *Thromb Haemost* 70:970-977). In comparing the activity of the factor VIIa-sTF complexes to the activity of the factor VIIa-AT complexes in the factor VIIa-AT standard, less than 5% of the initial activity should remain after heparin plus antithrombin treatment. If less than 5% of the original activity remains, then the concentration of factor VIIa-AT complexes in the final reaction mixture is considered to be equal to the starting factor VIIa concentration. The factor VIIa-AT standard was divided into 50 µl aliquots and frozen at −80° C.

On the day of use in the factor VIIa-AT ELISA assay, an aliquot of the factor VIIa-AT standard was thawed rapidly at 37° C. and then held at 4° C. until needed. Excess standard was discarded.

Assay

Anti-factor VII monoclonal antibody #1172 IgG (Antibody #1172; Morrissey lab; hybridomas deposited as ATCC No. PTA-3497) was diluted to 1 µg/ml in 0.1 M sodium carbonate buffer [Carbonate Buffer: 4.20 g sodium bicarbonate dissolved in 400 ml $H_2O$, adjusted to pH 9.2 with sodium hydroxide, and enough $H_2O$ added to give 500 ml final volume]. Antibody #1172 solution was pipetted at 0.1 ml per well into 96-well, flat-bottom ELISA plates (Costar EIA/RIA Plates, catalog #9018; Corning Inc., Corning, N.Y.) and incubated overnight at 4° C.

The wells were emptied by flicking the ELISA plate while upside-down. The wells were rinsed once with TBS/EDTA/Tween [TBS: 50 mM Tris.HCl buffer pH 7.4, 100 mM NaCl, and 0.1% w/v sodium azide; TBS/EDTA/Tween: TBS with 10 mM EDTA (diluted from 0.5M EDTA pH 7.4) and 0.1% v/v Tween-20].

The wells were filled with BLOTTO [BLOTTO: 5% w/v nonfat powdered milk in TBS] at approximately 0.3 ml per well. The plates were incubated 1 hour at 37° C. or overnight at 4° C. (Plates can be held in BLOTTO at this point of the protocol for at least a week at 4° C.) The wells were emptied by flicking the ELISA plate while upside-down. The wells were rinsed three times with TBS/EDTA/Tween.

Factor VIIa-AT standards and unknown samples (typically, citrated plasma samples) were diluted in TBS/EDTA/BSA [TBS/EDTA/BSA: TBS with with 10 mM EDTA (diluted from 0.5M EDTA pH 7.4) and 0.1% bovine serum albumin] as follows: plasma samples, diluted twenty- or forty-fold; Factor VIIa-AT standards for final concentrations per well of Factor VIIa-AT complexes of 0, 8, 16, 24, 32, 40, 48, and 56 pM. For each sample or standard, 0.1 ml was pipetted into duplicate wells. After incubating for 1 hour at 37° C., the wells were emptied by flicking the ELISA plate while upside-down. The wells were rinsed three times with TBS/EDTA/Tween.

Rabbit anti-human antithrombin III (polyclonal antibody; catalog #A0296; DAKO Corp, Carpinteria, Calif.) was diluted to 0.1 µg/ml in TBS/BSA/Tween [TBS/BSA/Tween: TBS with 0.1% w/v bovine serum albumin and 0.1% v/v Tween-20 and stored at 4° C.] and then pipetted into the wells at 0.1 ml per well. After incubating for 1 hour at 37° C., the wells were emptied by flicking the ELISA plate while upside-down. The wells were rinsed four times with TBS/Tween [TBS/Tween: TBS with 0.1% v/v Tween-20].

Donkey anti-rabbit IgG-alkaline phosphatase conjugate [Immunopure® Donkey Anti-rabbit IgG-alkaline (H+L), (min×BvChOtGuHaHnMsRtSh Sr Prot), Alkaline Phosphatase conjugated; catalog #31345; Pierce Chemical Co., Rockville, Ill.] was diluted to 0.25 µg/ml in TBS/BSA [TBS/BSA: TBS with 0.1% w/v bovine serum albumin] and then pipetted into the wells at 0.1 ml per well. After incubating for 1 hour at 37° C., the wells were emptied by flicking the ELISA plate while upside-down. The wells were rinsed four times with TBS/Tween.

Next, 100 µl p-NPP Solution [P-NPP Solution: p-NPP (1 mg/ml final) in p-NPP buffer (100 mM Tris-HCl pH 9.5, 100 mM NaCl, 5 mM $MgCl_2$, and 0.02% w/v sodium azide) just before use] was pipetted into each well. The ELISA plates were incubated at 37° C. for about 30 to 60 min, or until good color formation was seen in the standards. The ELISA plates were read in terms of absorbance at 405 nm using a 96-well plate reader. When it was necessary to delay taking absorbance readings, the reaction was stopped by adding 0.1 ml 0.1 M EDTA brought to pH 9.5 with NaOH per well.

A standard curve was prepared by plotting absorbance at 405 nm ($A_{405}$) versus Factor VIIa-AT concentration. The factor VIIa-AT levels of unknowns were then read from the standard curve. If the unknowns have $A_{405}$ values that were higher than the highest point on the standard curve, the test was repeated at a higher Factor VIIa-AT dilution.

EXAMPLE 2

ELISA for Factor VIIa-Antithrombin (VIIa-AT) Complexes (Without Blocking Agent)

Materials. The materials used in this example were as follows:

Anti-Factor VII Monoclonal Antibody—a calcium independent murine monoclonal antibody raised against human factor VII in the Morrissey lab, the hybridoma cells deposited as ATCC No. PTA-3497.

Anti-Human Antithrombin III Rabbit polyclonal antibody—DAKO catalog number A0296.

Bovine Serum Albumin—Calbiochem catalog number 12659 ("Albumin, bovine serum, fraction V, low heavy metals")

Donkey Anti-rabbit IgG (H+L), (min×BvChGtGuHaHsHnMsRtSh Sr Prot), Immunopure®, Alkaline Phosphatase Conjugated—Pierce catalog number 31345.

ELISA plates—Flat bottom Costar EIA/RIA Plates from Corning Inc. (Corning/Costar number 9018).

Factor VII-deficient plasma—Congenital factor VII-deficient plasma (citrated) from George King BioMedical, Inc. (www.kingbiomed.com)

pNPP (p-nitrophenyl phosphate)—Sigma catalog number N1891 (SIGMA FAST™ p-Nitrophenyl Phosphate Tablet Sets; 5 mg/tablet)

Solutions. Solutions used in the ELISA assay were prepared as follows. Unless otherwise noted, the solutions were stored at room temperature:

Carbonate Buffer: 0.1 M sodium carbonate buffer, pH 9.2. This is prepared by dissolving 4.20 g sodium bicarbonate in 400 ml $H_2O$; adjusting pH to 9.2 by adding 10 N NaOH dropwise. The final volume is brought to 500 ml with $H_2O$.

TBS: 50 mM Tris.HCl buffer pH 7.4; 100 mM NaCl; 0.02% w/v sodium azide

Washing Buffer: 0.1% Tween-20 in TBS

Sample Diluent: 0.1% w/v bovine serum albumin, 0.1% Tween-20, and 10 mM EDTA in TBS. Store at 4° C. (Use a pH 7.5 stock solution of EDTA to make this)

Antibody Diluent: 0.1% w/v bovine serum albumin and 0.1% Tween-20 in TBS. Store at 4° C.

PNPP Buffer: 100 mM Tris.HCl buffer pH 9.5; 100 mM NaCl; 5 mM $MgCl_2$; 0.02% w/v sodium azide pNPP Solution: Dissolve pNPP (1 mg/ml final) in pNPP Buffer just before use (one 5 mg tablet per 5 ml pNPP buffer)

Preparation of VIIa-AT Complexes for Standardizing the VIIa-AT ELISA.

Materials and Solutions

Antithrombin (Antithrombin III)—Haematologic Technologies, Inc. catalog number HCATIII-0120.

Bovine Serum Albumin—Calbiochem catalog number 12659 ("Albumin bovine serum, fraction V, low heavy metals")

Chromozym t-PA substrate—Roche Diagnostics catalog number 1 093 037

Factor VIIa (recombinant)—American Diagnostica catalog number 407recB.

Heparin—typically from Sigma (catalog number H9399); there are many other suppliers of heparin.

sTF—recombinant human soluble tissue factor (amino acids 1-219). (Morrissey, J. H. 1987. Cell 50:129-135).

HBSA/calcium: 30 mM Hepes buffer, pH 7.4; Store at 4° C. 100 mM NaCl; 5 mM $CaCl_2$; 0.1% w/v bovine serum albumin; 0.02% w/v sodium azide.

Procedure. This procedure can be scaled up to make larger stocks of factor VIIa-AT standards.

1. Prepare a 1.1 ml solution of 100 nM factor VIIa and 150 nM sTF in HBSA/calcium.

2. Remove a 0.1 ml aliquot and hold on ice.

3. To the remaining 1.0 ml reaction mixture, add heparin to a final concentration of 10 unit/ml and Antithrombin (Haematologic Technologies, Inc.) to a final concentration of 400 nM.

4. Incubate mixture at 37° C. for 60 minutes, then place mixture on ice.

5. Remove a small aliquot of each mixture (from Steps 2 and 4) and measure the remaining factor VIIa enzymatic activity (at a final concentration of 5 nM factor VIIa), using Chromozym t-PA substrate. (Neuenschwander P. F. et al. 1993. "Importance of substate composition, pH and other variables on tissue factor enhancement of factor VIIa activity," *Throm Haemost* 70:970-977). Compare the activity of the factor VIIa-sTF complexes in the aliquot removed in Step 2 to the activity remaining after incubating with heparin and antithrombin in Step 4. Expect to find less than 5% of the initial activity remaining after heparin plus antithrombin treatment. If this test is passed (less than 5% of the original activity remains), then consider the concentration of VIIa-AT complexes in the final reaction mixture to be equal to the starting factor VIIa concentration.

6. Divide the stock into 50 µl aliquots and freeze at −80° C.

7. On the day of use, thaw an aliquot of VIIa-AT standards rapidly at 37° C. and then hold at 4° C. until needed. Discard excess; do not re-freeze.

Washing Techniques

Washing the ELISA plate wells may be accomplished either by hand or by using automated ELISA plate washers. Exemplary suitable techniques for automated washers are as follows. For the Skan Washer 300 automated ELISA plate washer, we have used three cycles of Aspirate 2.5 sec, Wash 400 NI, Soak 15 sec, followed by a 8 sec final aspiration For the MultiWash Advantage commercial automated ELISA plate washer, we used three cycles of 0.8 ml wash with the following other settings: speed=45; soak=60 sec; mode=plate wash; bottom wash=off and crosswise aspiration=on.

For hand washing, first empty the wells by "flicking" the plate upside-down in the sink. Then, fill the wells with wash solution dispensed by a squeeze bottle. (Avoid generating bubbles.) When all of the wells are filled, empty the plate again by "flicking" and start the process over. At the end of the third wash, empty the wells completely by repeatedly rapping the plate upside-down on several paper towels on the lab bench. Do this until the wells have no visible liquid in them.

Assay

In this example, Anti-factor VII monoclonal antibody was diluted to 1 µg/ml in Carbonate Buffer. 0.1 ml was pipetted into each well of a an ELISA plates and incubated overnight at 4° C. The wells were then rinsed three times with Washing Buffer.

VIIa-AT standards were removed from storage in the freezer, thawed rapidly at 37° C., then placed on ice until ready for use. Excess standards not used in the ELISA were discarded. (The standards should not be reused or refrozen, but discarded). 10 µl of 100 nM VIIa-AT standards was diluted into 10 ml Sample Diluent (resulting in a 100 pM stock). Then, the 100 pM stock was diluted further as follows in Table III.

TABLE III

Dilution of VIIa-AT Standards

| Final conc | µl 100 PM stock | µl Sample Diluent |
|---|---|---|
| 0 pM | 0 | 300 |
| 5 pM | 15 | 285 |
| 10 pM | 30 | 270 |
| 15 pM | 45 | 255 |
| 20 pM | 60 | 240 |
| 25 pM | 75 | 225 |
| 30 pM | 90 | 210 |

Unknown samples (citrated plasma samples) were diluted twenty fold in Sample Diluent. This was accomplished by adding 15 µl test plasma to 285 µl Sample Diluent.

For each sample or standard, 0.1 ml of the dilutions described above were pipetted into each of two wells and incubated 1 hour at 37° C. After incubation, the wells were rinsed three times with Washing Buffer.

Rabbit anti-human antithrombin III (DAKO) was diluted to 0.1 µg/ml in Antibody Diluent as follows. For 1.3 mg/ml stock solution, 3 µl was mixed with 36 µl Antibody Diluent to give 100 µg/ml IgG antibody. Then, 12 µl of diluted antibody was mixed with 12 ml Antibody Diluent to give 0.1 µg/ml. 0.1 ml per well of 0.1 µg/ml rabbit anti-human antithrombin III antibody was added and incubated 1 hour at 37° C. The wells were then rinsed three times with Washing Buffer.

Donkey anti-rabbit IgG-alkaline phosphatase conjugate was diluted to 0.25 µg/ml in Antibody Diluent as follows. For a 600 µg/ml stock solution, 5 µl was mixed with 12 ml Antibody Diluent to give 0.25 µg/ml IgG. 0.1 ml was added to each well and incubated 1 hour at 37° C. The wells were then rinsed three times with Washing Buffer.

100 µl of pNPP Solution was then pipetted into each well. The plates were incubated about 30 to 60 min at 37° C. (until good color formation was seen in the standards-sometimes it takes longer). The highest standard (30 pM) should have an $A_{405}$ of about 1.5.

The absorbance was read at 405 nm in a 96-well plate reader. If desired, the reaction may be stopped by adding 0.1 ml 0.1 M EDTA (brought to pH 9.5 with NaOH) per well. Stopping the reaction is only necessary if one wishes to delay reading.

A standard curve was prepared by plotting absorbance at 405 nm versus VIIa-AT concentration. The VIIa-AT levels of unknowns were then read from the standard curve. The plate was read on a Molecular Devices SPECTRAmax PLUS 384 microplate reader (no back-ground subtraction) and a second-order polynomial was fit to the data. The standard curve can be seen at FIG. 5.

I claim:

1. A method of measuring the concentration of factor VIIa-antithrombin complexes circulating in a patients plasma, comprising:

mixing a quantity of a plasma sample from said patient with a primary capture antibody fixed to a solid phase, wherein said capture antibody specifically binds ability to bind, independent of the presence or absence of calcium ions, to the factor VIIa portion of factor VIIa-antithrombin complexes which is present in said plasma sample, and incubating said mixture under conditions to promote binding between said capture antibody and said factor VIIa-antithrombin complexes in said plasma sample to form capture antibody-factor VIIa-antithrombin complexes and unbound components in the mixture;

removing said unbound components;

mixing said capture antibody-factor VIIa-antithrombin complexes with a secondary antibody having the ability to bind to the antithrombin portion of said capture antibody-factor VIIa-antithrombin complexes to form capture antibody-factor VIIa-antithrombin-secondary antibody complexes and unbound components in the mixture;

removing any unbound components; and determining the amount of capture antibody-factor VIIa-antithrombin-secondary antibody complexes by comparing the amount of capture antibody-factor VIIa-antithrombin-secondary antibody complexes to a standard amount of capture antibody-factor VIIa-antithrombin-secondary antibody complexes determined for factor VIIa-antithrombin complexes of a known concentration.

2. The method of claim 1, wherein said standard amount of capture antibody-factor VIIa-antithrombin-secondary antibody complexes is determined for a plurality of known concentrations of factor VIIa-antithrombin complexes by mixing a quantity of said known concentration of factor VIIa-antithrombin complexes with a primary capture antibody that specifically binds ability to bind to the factor VIIa portion of factor VIIa-antithrombin complexes and incubating said mixture under conditions to promote binding between said capture antibody and said factor VIIa-antithrombin complexes to form capture antibody-factor VIIa-antithrombin complexes;

removing any unbound components; mixing said capture antibody-factor VIIa-antithrombincomplexes with a secondary antibody having the ability to bind to the antithrornbin portion of said capture antibody-factor VIIa-antithrombin complexes; removing any unbound components; and correlating said known concentrations of factor VIIa-antithrombin complexes with said amount of capture antibody-factor VIIa-antithrombin-secondary antibody complexes to form a standard curve.

3. The method of claim 1 or 2, wherein said secondary antibody is detectable by means of a label selected from the group consisting of enzyme label, radioisotopic label, nonradioactive label, fluorescent label, toxin label, and chemiluminescent label.

4. The method of claim 1 or 2, wherein a tertiary antibody having the ability to bind to said bound secondary antibody is reacted with said capture antibody-factor VIIa-antithrombin-secondary antibody complexes, said tertiary antibody being detectable by means of a label selected from the group consisting of enzyme label, radioisotopic label, nonradioactive label, fluorescent label, toxin label, and chemiluminescent label.

5. The method of claim 1, wherein said capture antibody is a monoclonal antibody produced by hybridoma cell ATCC No. PTA 3497.

6. The method of claim 1, wherein said standard is from about 0 to 100 picomoles.

7. A method of measuring the concentration of factor VIIa-antithrombin complexes circulating in a patient's plasma, comprising:

mixing a quantity of a plasma sample from said patient with a primary capture antibody fixed to a solid phase, said capture antibody having the ability to bind to the antithrpmbin portion of factor VIIa-antithrombin complexes which is present in said plasma sample, and incubating said mixture under conditions to promote binding between said capture antibody and said factor VIIa-antithrombin complexes to form capture antibody-factor VIIa-antithrombin complexes and unbound components in the mixture;

removing unbound components;

mixing said capture antibody-factor VIIa-antithrombin complexes with a secondary antibody which specifically binds ability to bind, independent of the presence or absence of calcium ions, to the factor VIIa portion of said capture antibody-factor VIIa-antithrombin complexes to form capture antibody-factor VIIa-antithrombin-secondary antibody complexes and unbound components in the mixture;

removing any unbound components;

determining the amount of capture antibody-factor VIIa-antithrombin-secondary antibody complexes; and comparing the amount of capture antibody-factor VIIa-antithrombin-secondary antibody complexes to a standard amount of capture antibody-factor VIIa-antithrombin-secondary antibody complexes determined for factor VIIa-antithrombin complexes of a known concentration.

8. The method of claim 7, wherein said standard amount of capture antibody-factor VIIa-antithrombin-secondary antibody complexes is determined for a plurality of known concentrations of factor VIIa-antithrombin complexes-by mixing a quantity of said known concentration of factor VIIa-antithrombin complexes with a primary capture antibody having the ability to bind to the antithrombin portion of factor VIIa-antithrombin complexes and incubating said mixture under conditions to promote binding between said capture antibody and said factor VIIa-antithrombin complexes to form capture antibody- factor VIIa-antithrombin complexes; removing any unbound components; mixing said capture antibody-factor VIIa-antithrombin complexes with a secondary antibody that specifically binds ability to bind to the factor VIIa portion of said capture antibody-factor VIIa-antithrombin complexes; removing any unbound components; determining the amount of capture antibody-factor VIIa-antithrombin-secondary antibody complexes and correlating said known concentrations of factor VIIa-antithrombin complexes with said amount of capture antibody-factor VIIa-antithrombin-secondary antibody complexes to form a standard curve.

9. The method of claim 7 or 8, wherein said capture antibody- factor VIIa-antithrombin-secondary antibody complexes are detectable by means of a label selected from the group consisting of enzyme label, radioisotopic label, nonradioactive label, fluorescent label, toxin label, and chemiluminescent label.

10. The method of claim 7 or 8, wherein a tertiary antibody having the ability to bind to said capture antibody-factor VIIa-antithrombin-secondary antibody complexes is mixed therewith, said tertiary antibody being detectable by means of a label selected from the group consisting of enzyme label, radioisotopic label, nonradioactive label, fluorescent label, toxin label, and chemiluminescent label.

11. The method of claim 7, wherein said secondary antibody is a monoclonal antibody produced by hybridoma cell ATCC No. PTA 3497.

12. The method of claim 7, wherein said standard is from about 0 to 100 picomoles.

13. A monoclonal antibody having the ability to bind to factor VII/VIIa in the absence of calcium ions and the ability to bind to non-denatured factor VIIa that is in complex with antithrombin.

14. A reagent for a method for testing for factor VIIa-antithrombin complexes, said reagent comprising a monoclonal antibody having the ability to bind to a factor VIIa-antithrombin complex in the absence of calcium ions.

15. A hybridoma cell ATCC No. PTA 3497.

16. A monoclonal antibody produced by hybridoma cell ATCC No. PTA 3497.

* * * * *

UNITED STATES PATENT AND TRADEMARK OFFICE
CERTIFICATE OF CORRECTION

PATENT NO. : 7,494,782 B2
APPLICATION NO. : 10/481345
DATED : February 24, 2009
INVENTOR(S) : James H. Morrissey It is certified that error appears in the above-identified patent and that said Letters Patent is hereby corrected as shown below:

In the Drawings: Delete Figure 3 and replace with the Figure 3 below.

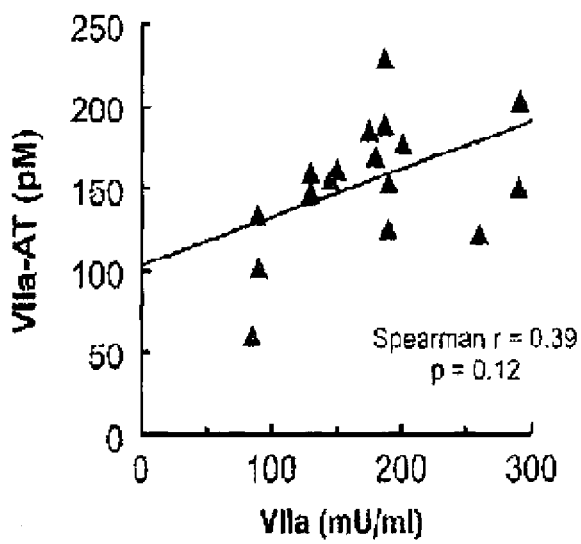

FIG. 3

Col. 2, line 28, replace, "12:387406" with -- 12:387-406 --
Col. 2, line 60, change "are" to -- is --
Col. 3, line 67, replace, "in plasma Antibodies for" with -- in plasma. Antibodies for --
Col. 5, line 44-45, replace, "anti-VII a" with -- anti-VII/VIIa --
Col. 5, line 46, replace, "Example 1 and 2" with -- Examples 1 and 2 --
Col. 6, line 53, replace, "according the procedures" with -- according to the procedures --
Col. 8, lines 12-13, replace, "substrate p-nitrophenylphosphate p-NPP)" with
-- substrate $p$-nitrophenylphosphate ($p$-NPP) --
Col. 9, line 62, replace, "p-NPP" with -- $p$-NPP --

Signed and Sealed this
Fourteenth Day of August, 2012

David J. Kappos
*Director of the United States Patent and Trademark Office*

Col. 10, line 59, replace, "Tris.HCl buffer" with -- Tris•HCl buffer --
Col. 11, line 5, replace, "TBS with with 10 mM EDTA" with -- TBS with 10 mM EDTA --
Col. 11, line 26, replace, "(min×BvChOtGuHaHsHnMsRtSh Sr Prot)" with
-- (min × BvChGtGuHaHsHnMsRtSh Sr Prot) --
Col. 11, lines 34-35, replace, "p-NPP Solution [P-NPP Solution: p-NPP (1 mg/ml final) in p-NPP buffer" with -- *p*-NPP Solution [*p*-NPP Solution: *p*-NPP (1 mg/ml final) in *p*-NPP buffer --
Col. 11, line 61, replace, "factorVII" with -- factor VII --
Col. 12, lines 1-2, replace, "(min×BvChOtGuHaHsHnMsRtSh Sr Prot)" with
-- (min × BvChGtGuHaHsHnMsRtSh Sr Prot) --
Col 12, line 20, replace, "50 mM Tris.HCl buffer" with -- 50 mM Tris•HCl buffer --
Col. 13, line 37, replace, "well of a an ELISA plates" with -- well of an ELISA plate --
Col. 14, line 12, replace, "0.25 μg/ml IgG.0.1 ml was added" with -- 0.25 μg/ml IgG. 0.1 ml was added --
Col. 20, line 27, replace, "PNPP Buffer: 100 mM Tris.HCl buffer" with -- pNPP Buffer: 100 mM Tris•HCl buffer --
Claim 1, lines 1-2 , before "antithrombin", change "VIa-" to -- VIIa- --
Claim 1, line 2, replace, "patients" with -- patient's --
Claim 1, lines 6-7, delete, "ability to bind"
Claim 2, line 7, delete, "ability to bind"
Claim 2, line 13, replace, "antithrombincomplexes" with -- antithrombin complexes --
Claim 2, line 15, replace, "antithrornbin" with -- antithrombin --
Claim 7, line 7, replace, "antithrpmbin" with -- antithrombin --
Claim 7, line 17, delete, "ability to bind"
Claim 8, line 14, delete, "ability to bind"

UNITED STATES PATENT AND TRADEMARK OFFICE
CERTIFICATE OF CORRECTION

PATENT NO. : 7,494,782 B2
APPLICATION NO. : 10/481345
DATED : February 24, 2009
INVENTOR(S) : James H. Morrissey It is certified that error appears in the above-identified patent and that said Letters Patent is hereby corrected as shown below:

In the Drawings: Delete Figure 3 and replace with the Figure 3 below.

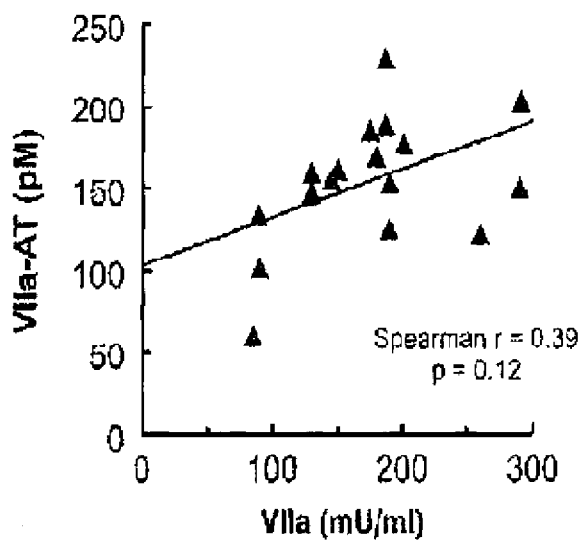

Col. 2, line 28, replace, "12:387406" with -- 12:387-406 --
Col. 2, line 60, change "are" to -- is --
Col. 3, line 67, replace, "in plasma Antibodies for" with -- in plasma. Antibodies for --
Col. 5, line 44-45, replace, "anti-VII a" with -- anti-VII/VIIa --
Col. 5, line 46, replace, "Example 1 and 2" with -- Examples 1 and 2 --
Col. 6, line 53, replace, "according the procedures" with -- according to the procedures --

This certificate supersedes the Certificate of Correction issued August 14, 2012.

Signed and Sealed this
Fourth Day of September, 2012

David J. Kappos
*Director of the United States Patent and Trademark Office*

CERTIFICATE OF CORRECTION (continued)
U.S. Pat. No. 7,494,782 B2

Col. 8, lines 12-13, replace, "substrate p-nitrophenylphosphate p-NPP)" with
-- substrate *p*-nitrophenylphosphate (*p*-NPP) --
Col. 9, line 62, replace, "p-NPP" with -- *p*-NPP --
Col. 10, line 59, replace, "Tris.HCl buffer" with -- Tris•HCl buffer --
Col. 11, line 5, replace, "TBS with with 10 mM EDTA" with -- TBS with 10 mM EDTA --
Col. 11, line 26, replace, "(min×BvChOtGuHaHsHnMsRtSh Sr Prot)" with
-- (min × BvChGtGuHaHsHnMsRtSh Sr Prot) --
Col. 11, lines 34-35, replace, "p-NPP Solution [P-NPP Solution: p-NPP (1 mg/ml final) in p-NPP buffer" with -- *p*-NPP Solution [*p*-NPP Solution: *p*-NPP (1 mg/ml final) in *p*-NPP buffer --
Col. 11, line 61, replace, "factorVII" with -- factor VII --
Col. 12, lines 1-2, replace, "(min×BvChOtGuHaHsHnMsRtSh Sr Prot)" with
-- (min × BvChGtGuHaHsHnMsRtSh Sr Prot) --
Col 12, line 20, replace, "50 mM Tris.HCl buffer" with -- 50 mM Tris•HCl buffer --
Col. 13, line 37, replace, "well of a an ELISA plates" with -- well of an ELISA plate --
Col. 14, line 12, replace, "0.25 µg/ml IgG.0.1 ml was added" with -- 0.25 µg/ml IgG. 0.1 ml was added --
Col. 20, line 27, replace, "PNPP Buffer: 100 mM Tris.HCl buffer" with -- pNPP Buffer: 100 mM Tris•HCl buffer --
Column 14, lines 33-34 (Claim 1, lines 1-2) before "antithrombin", change "Vila-" to -- VIIa- --
Column 14, line 34 (Claim 1, line 2) replace, "patients" with -- patient's --
Column 15, lines 38-39 (Claim 1, lines 6-7) delete, "ability to bind"
Column 15, line 2 (Claim 2, line 7) delete, "ability to bind"
Column 15, line 8 (Claim 2, line 13) replace, "antithrombincomplexes" with
-- antithrombin complexes --
Column 15, line 10 (Claim 2, line 15) replace, "antithrornbin" with -- antithrombin --
Column 15, line 40 (Claim 7, line 7) replace, "antithrpmbin" with -- antithrombin --
Column 15, line 50 (Claim 7, line 17) delete, "ability to bind"
Column 16, line 20 (Claim 8, line 14) delete, "ability to bind"

UNITED STATES PATENT AND TRADEMARK OFFICE
CERTIFICATE OF CORRECTION

| | | |
|---|---|---|
| PATENT NO. | : 7,494,782 B2 | |
| APPLICATION NO. | : 10/481345 | |
| DATED | : February 24, 2009 | |
| INVENTOR(S) | : James H. Morrissey | |

It is certified that error appears in the above-identified patent and that said Letters Patent is hereby corrected as shown below:

In the Drawings: Delete Figure 3 and replace with the Figure 3 below.

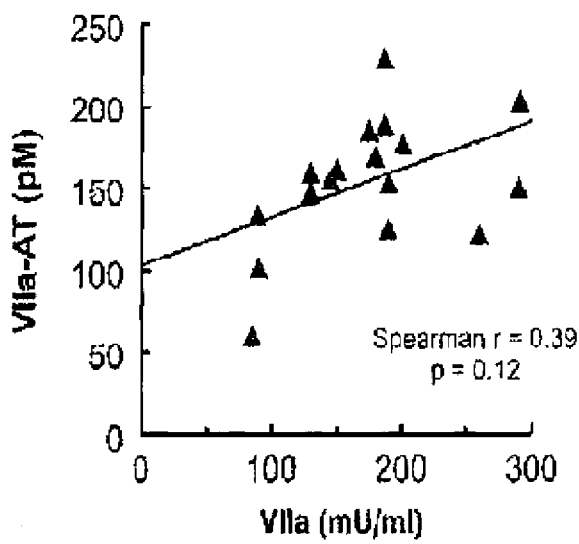

FIG. 3

Col. 2, line 28, replace, "12:387406" with -- 12:387-406 --
Col. 2, line 60, change "are" to -- is --
Col. 3, line 67, replace, "in plasma Antibodies for" with -- in plasma. Antibodies for --
Col. 5, line 44-45, replace, "anti-VII a" with -- anti-VII/VIIa --
Col. 5, line 46, replace, "Example 1 and 2" with -- Examples 1 and 2 --
Col. 6, line 53, replace, "according the procedures" with -- according to the procedures --

This certificate supersedes the Certificates of Correction issued August 14, 2012 and September 4, 2012.

Signed and Sealed this
Ninth Day of October, 2012

David J. Kappos
*Director of the United States Patent and Trademark Office*

CERTIFICATE OF CORRECTION (continued)
U.S. Pat. No. 7,494,782 B2

Col. 8, lines 12-13, replace, "substrate p-nitrophenylphosphate p-NPP)" with
-- substrate *p*-nitrophenylphosphate (*p*-NPP) --
Col. 9, line 62, replace, "p-NPP" with -- *p*-NPP --
Col. 10, line 59, replace, "Tris.HCl buffer" with -- Tris•HCl buffer --
Col. 11, line 5, replace, "TBS with with 10 mM EDTA" with -- TBS with 10 mM EDTA --
Col. 11, line 26, replace, "(min×BvChOtGuHaHsHnMsRtSh Sr Prot)" with
-- (min × BvChGtGuHaHsHnMsRtSh Sr Prot) --
Col. 11, lines 34-35, replace, "p-NPP Solution [P-NPP Solution: p-NPP (1 mg/ml final) in p-NPP buffer" with -- *p*-NPP Solution [*p*-NPP Solution: *p*-NPP (1 mg/ml final) in *p*-NPP buffer --
Col. 11, line 61, replace, "factorVII" with -- factor VII --
Col. 12, lines 1-2, replace, "(min×BvChOtGuHaHsHnMsRtSh Sr Prot)" with
-- (min × BvChGtGuHaHsHnMsRtSh Sr Prot) --
Col 12, line 20, replace, "50 mM Tris.HCl buffer" with -- 50 mM Tris•HCl buffer --
Col. 13, line 37, replace, "well of a an ELISA plates" with -- well of an ELISA plate --
Col. 14, line 12, replace, "0.25 µg/ml IgG.0.1 ml was added" with -- 0.25 µg/ml IgG. 0.1 ml was added --
Col. 20, line 27, replace, "PNPP Buffer: 100 mM Tris.HCl buffer" with -- pNPP Buffer: 100 mM Tris•HCl buffer --
Column 14, lines 33-34 (Claim 1, lines 1-2) before "antithrombin", change "VIIa-" to -- VIIa- --
Column 14, line 34 (Claim 1, line 2) replace, "patients" with -- patient's --
Column 14, lines 38-39 (Claim 1, lines 6-7) delete, "ability to bind"
Column 15, line 2 (Claim 2, line 7) delete, "ability to bind"
Column 15, line 8 (Claim 2, line 13) replace, "antithrombincomplexes" with
-- antithrombin complexes --
Column 15, line 10 (Claim 2, line 15) replace, "antithrornbin" with -- antithrombin --
Column 15, line 40 (Claim 7, line 7) replace, "antithrpmbin" with -- antithrombin --
Column 15, line 50 (Claim 7, line 17) delete, "ability to bind"
Column 16, line 20 (Claim 8, line 14) delete, "ability to bind"